US00PP11726P

United States Patent [19]

Atchison

[11] Patent Number: Plant 11,726

[45] Date of Patent: Dec. 26, 2000

[54] SCHEFFLERA PLANT NAMED 'CONNIE'

[76] Inventor: James Kyle Atchison, 9625 Happy Hollow Rd., Delray Beach, Fla. 33446

[21] Appl. No.: 09/250,013

[22] Filed: Feb. 12, 1999

[51] Int. Cl.[7] ..... A01H 5/00

[52] U.S. Cl. ..... Plt./377

[58] Field of Search ..... Plt./377

*Primary Examiner*—Bruce R. Campell
*Assistant Examiner*—Wendy A. Baker
*Attorney, Agent, or Firm*—C. A. Whealy

[57] ABSTRACT

A distinct cultivar of Schefflera plant named Connie, characterized by its upright and columnar plant habit; closely-spaced leaves and very short petioles which give a dense and full appearance; and very dark green and glossy leaflets that are thick and leathery.

2 Drawing Sheets

BACKGROUND OF THE INVENTION

The present invention relates to a new and distinct cultivar of Schefflera plant, botanically known as *Brassaia actinophylla*, and hereinafter referred to by the cultivar name Connie.

The new Schefflera was discovered by the Inventor in a controlled environment in Delray Beach, Fl., in October, 1994, as a naturally-occurring mutation of an unidentified selection of *Brassaia actinophylla*. The new Schefflera was observed as a single plant in a group of plants of the parent selection.

Plants of the new Schefflera differ from the parent selection in the following characteristics:

1. Plants of the new Schefflera are columnar in growth habit whereas plants of the parent selection are outwardly spreading.
2. Plants of the new Schefflera have much shorter leaf petioles than plants of the parent selection.

Asexual propagation of the new Schefflera by air layers and tissue culture has shown that the unique features of this new Schefflera are stable and reproduced true to type in successive generations.

The new Schefflera has not been observed under all possible environmental conditions. The phenotype may vary somewhat with variations in environment such as temperature and light intensity, without, however, any variance in genotype.

SUMMARY OF THE INVENTION

The following traits have been repeatedly observed and are determined to be the unique characteristics of plants of the new Schefflera. These characteristics in combination distinguish the new Schefflera as a new and distinct cultivar:

1. Upright and columnar plant habit.
2. Closely-spaced leaves and very short petioles which give a dense and full appearance.
3. Very dark green and glossy leaflets that are thick and leathery.

BRIEF DESCRIPTION OF THE PHOTOGRAPHS

The accompanying colored photographs illustrate the overall appearance of the new Schefflera, showing the colors as true as it is reasonably possible to obtain in colored reproductions of this type.

The photograph on the first sheet comprises a side perspective view of a typical potted plant of the new Schefflera.

The photograph at the top of the second sheet comprises a close-up view of typical young leaves of the new Schefflera.

The photograph at the bottom of the second sheet comprises a close-up view of typical mature leaves of the new Schefflera. Leaf colors in the photographs may differ from actual colors due to light reflectance caused by the glossiness of the leaves.

DETAILED BOTANICAL DESCRIPTION

The new Schefflera has not been observed under all possible environmental conditions. The phenotype may vary somewhat with variations in environment such as temperature and light intensity, without, however, any variance in genotype.

In the following description, color references are made to The Royal Horticultural Society Colour Chart except where general terms of ordinary dictionary significance are used. The following observations and measurements describe 18 month old plants grown in 33-cm containers grown in Delray Beach, Fla., under commercial greenhouse practice.

Botanical classification: *Brassaia actinophylla* cultivar Connie.

Parentage: Naturally-occurring mutation of an unidentified selection of *Brassaia actinophylla.*

Propagation:

*Type.*—By terminal cuttings.

*Time to initiate roots.*—Winter: About 3 to 4 weeks at 21° C. Summer: About 2 to 3 weeks at 27° C.

*Time to produce a rooted cutting.*—About 6 to 8 weeks.

*Rooting habit.*—Numerous, fleshy and thick.

Plant description:

*Plant type.*—Tropical evergreen tree.

*Plant shape.*—Upright, columnar, symmetrical.

*Growth habit.*—Bushy, dense and full.

*Plant height.*—About 170 cm from soil level to top of leaf plane.

*Plant vigor/crop time.*—Relatively rapid growth rate under optimum temperatures. Appropriate for 24-cm and larger containers.

*Stem description.*—Shape: Nearly round with lenticels about 8 mm in length. Diameter: At plant base, about 3.5 cm. Internode length: Usually about 6 cm or less. Color: 144A; base, woody, tan in color.

*Foliage description.*—Radially compound leaves. Number of leaflets per leaf: Usually about seven or eight. Leaf diameter: About 48 cm. Leaf petiole: Cross-section: Round. Length: Short, about 2.5 cm. Diameter: About 1.5 cm or thicker. Color: 144A.

Leaflet shape: Oblong. Leaflet length: About 27 cm. Leaflet width: About 14 cm. Margin: Entire. Leaflet apex: Apiculate. Leaflet base: Cuneate to obtuse. Leaflet texture: Leathery, thick, smooth, very glossy, glabrous and durable. Leaflet color: Young leaves, upper surface: Very glossy, close to 137A. Young leaves, lower surface: Close to 147B. Mature leaves, upper surface: Glossy, darker than 137A. Mature leaves, lower surface: Close to 147B. Venation, upper surface: Close to 144B. Venation, lower surface: Close to 147C. Leaflet petiole: Cross-section: Mostly rounded. Length: About 4.8 cm. Diameter: About 5 mm or thicker. Color: 144A.

Flower description: Flowers have not been observed on plants of the new Schefflera.

Disease resistance: Resistance to known Schefflera pathogens has not been observed on plants grown under commercial production conditions.

It is claimed:

1. A new and distinct cultivar of Schefflera plant named Connie, as illustrated and described.

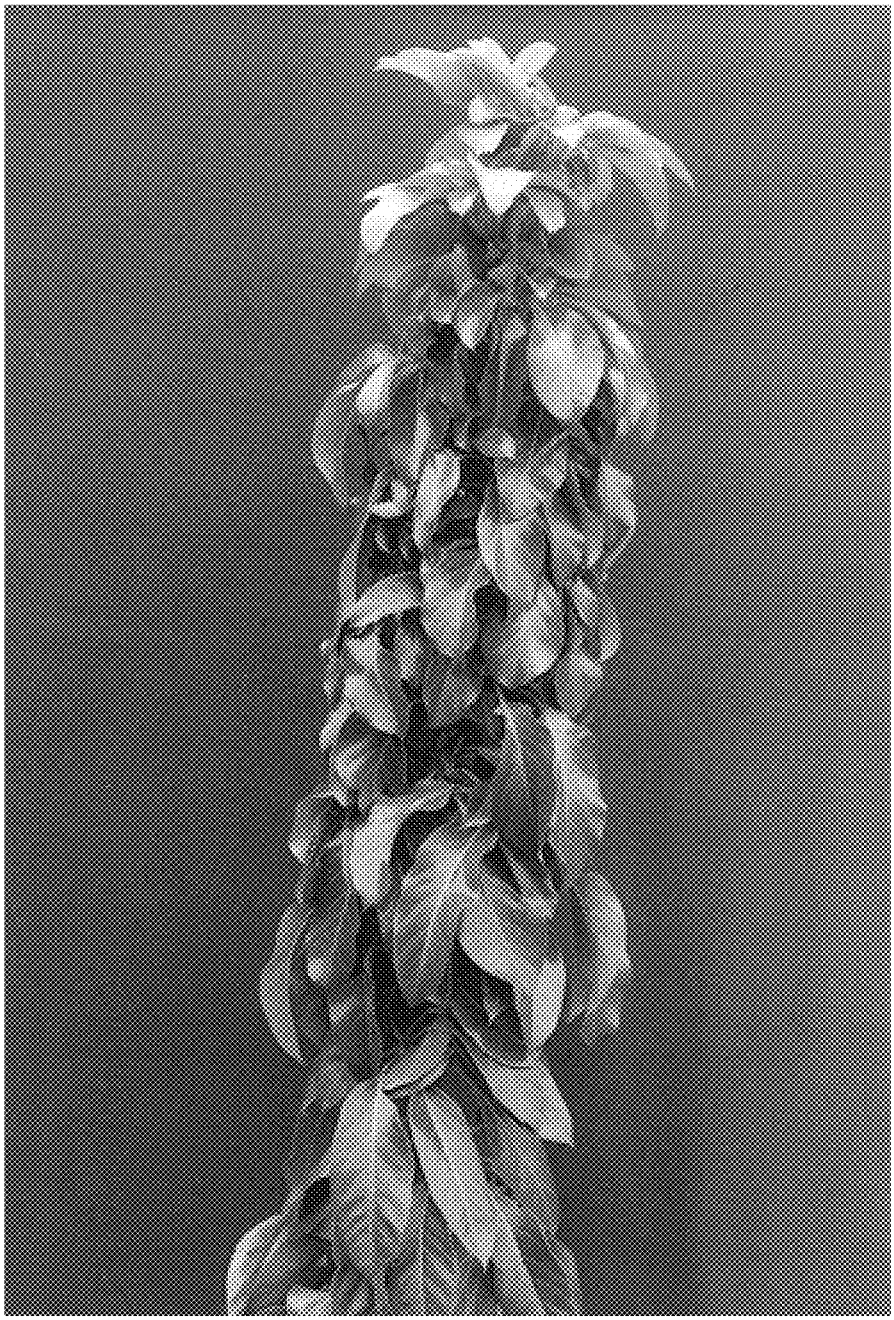

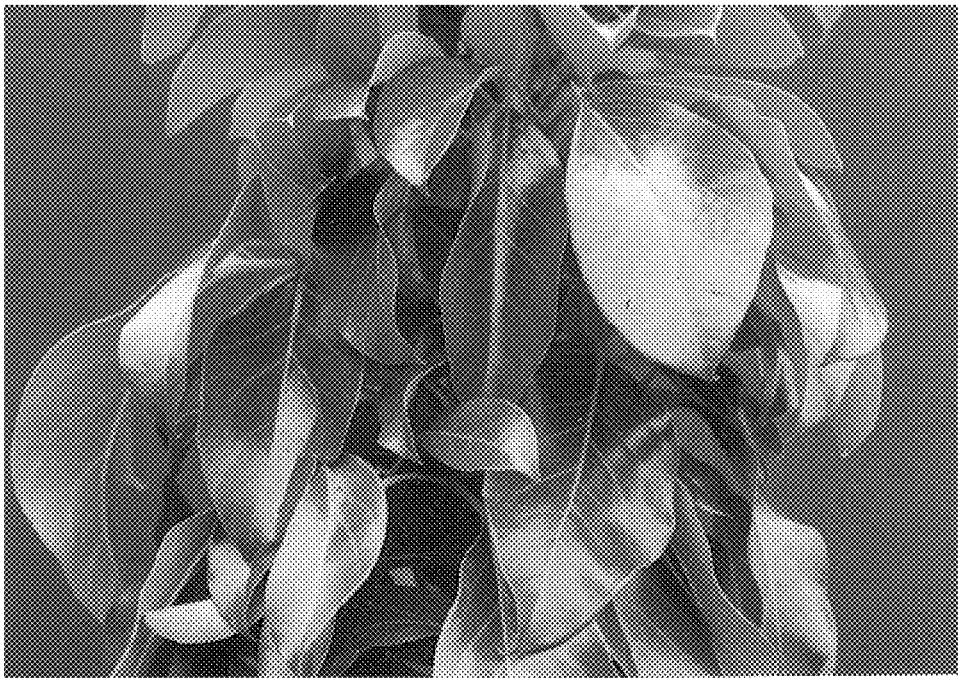
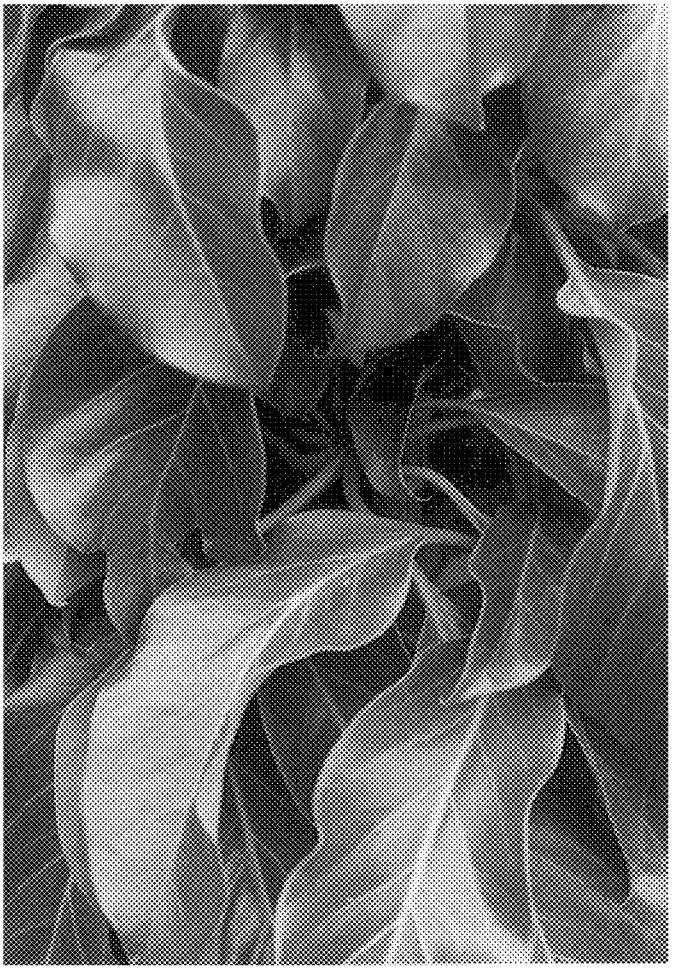

* * * * *